US00PP25121P2

(12) United States Plant Patent
Miedema-Jorna

(10) Patent No.: US PP25,121 P2
(45) Date of Patent: Nov. 25, 2014

(54) ***PETUNIA* PLANT NAMED 'FIPETFANANGEL'**

(50) Latin Name: *Petunia×hybrida*
Varietal Denomination: Fipetfanangel

(71) Applicant: Anita Miedema-Jorna, De Lier (NL)

(72) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 76 days.

(21) Appl. No.: 13/815,278

(22) Filed: Feb. 15, 2013

(51) Int. Cl.
*A01H 5/00* (2006.01)

(52) U.S. Cl.
USPC ..... Plt./356.13

(58) Field of Classification Search
CPC ..... A01H 5/00
USPC ..... Plt./356.13
See application file for complete search history.

*Primary Examiner* — Anne Grunberg
(74) *Attorney, Agent, or Firm* — C. A. Whealy

(57) ABSTRACT

A new and distinct cultivar of *Petunia* plant named 'Fipetfanangel', characterized by its outwardly spreading and mounding growth habit; freely branching habit; freely flowering habit; red purple-colored flowers with very light pink to almost white-colored centers; and good garden performance.

1 Drawing Sheet

Botanical designation: *Petunia×hybrida*.
Cultivar denomination: 'FIPETFANANGEL'.

BACKGROUND OF THE INVENTION

The present invention relates to a new and distinct *Petunia* plant, botanically known as *Petunia×hybrida* and hereinafter referred to by the name 'Fipetfanangel'.

The new *Petunia* plant is a product of a planned breeding program conducted by the Inventor in De Lier, The Netherlands. The objective of the breeding program is to create new freely-branching *Petunia* plants with early and freely flowering habit, and attractive flower color.

The new *Petunia* plant originated from a cross-pollination made by the Inventor in 2010 in De Lier, The Netherlands of a proprietary selection of *Petunia×hybrida* identified as code number For 111020, not patented, as the female, or seed parent with a proprietary selection of *Petunia×hybrida* identified as code number For 111021. The new *Petunia* plant was discovered and selected by the Inventor as a single flowering plant within the progeny of the stated cross-pollination in a controlled greenhouse environment in De Lier, The Netherlands in 2011.

Asexual reproduction of the new *Petunia* plant by terminal cuttings in a controlled greenhouse environment in De Lier, The Netherlands since 2011 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Fipetfanangel'. These characteristics in combination distinguish 'Fipetfanangel' as a new and distinct *Petunia* plant:

1. Outwardly spreading and mounding growth habit.
2. Freely branching habit.
3. Freely flowering habit.
4. Red purple-colored flowers with very light pink to almost white-colored centers.
5. Good garden performance.

Plants of the new *Petunia* can be compared to plants of the female parent selection. Plants of the new *Petunia* differ from plants of the female parent selection in plant habit as plants of the new *Petunia* are not as upright as plants of the female parent selection.

Plants of the new *Petunia* can be compared to plants of the male parent selection. Plants of the new *Petunia* differ from plants of the male parent selection in the following characteristics:

1. Plants of the new *Petunia* are not as upright as plants of the male parent selection.
2. Plants of the new *Petunia* and the male parent selection differ in flower color.

Plants of the new *Petunia* can be compared to plants of *Petunia×hybrida* 'Famous Dark Pink Morn', not patented. In side-by-side comparisons conducted in De Lier, The Netherlands, plants of the new *Petunia* differed from plants of 'Famous Dark Pink Morn' in the following characteristics:

1. Plants of the new *Petunia* were more compact than and not as upright as plants of 'Famous Dark Pink Morn'.
2. Plants of the new *Petunia* and 'Famous Dark Pink Morn' differed in flower color as plants of 'Famous Dark Pink Morn' had darker red purple-colored flowers with white-colored centers.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant. The photograph comprises a side perspective view of a typical flowering plant of 'Fipetfanangel' grown in a container.

DETAILED BOTANICAL DESCRIPTION

The aforementioned photograph and following observations, measurements and values describe plants grown during the autumn and winter in 10.5-cm containers in a glass-covered greenhouse in De Lier, The Netherlands. During the production of the plants, day and night temperatures averaged 18° C. Plants were ten weeks old when the photograph and description were taken. In the following description, color references are made to The Royal Horticultural Society Colour Chart, 2007 Edition, except where general terms of ordinary dictionary significance are used.

Botanical classification: *Petunia×hybrida* 'Fipetfanangel'.

Parentage:

*Female, or seed, parent*.—Proprietary selection of *Petunia×hybrida* identified as code number For 111020.

*Male, or pollen, parent*.—Proprietary selection of *Petunia×hybrida* identified as code number For 111021.

Propagation:

*Type*.—By terminal cuttings.

*Time to initiate roots, summer*.—About five to seven days at temperatures of 19° C. to 20° C.

*Time to initiate roots, winter*.—About six to eight days at temperatures of 19° C. to 20° C.

*Time to produce a rooted young plant, summer*.—About 14 to 19 days at temperatures of 19° C. to 20° C.

*Time to produce a rooted young plant, winter*.—About 14 to 21 days at temperatures of 19° C. to 20° C.

*Root description*.—Fine; white in color.

*Rooting habit*.—Freely branching; moderately dense.

Plant description:

*Plant and growth habit*.—Outwardly spreading and mounding growth habit; moderately vigorous growth habit.

*Branching habit*.—Freely branching habit with about six primary lateral branches each with multiple secondary lateral branches; pinching is typically not required.

*Plant height*.—About 15 cm.

*Plant diameter*.—About 23 cm.

Lateral branch description:

*Length*.—About 15 cm.

*Diameter*.—About 3 mm.

*Internode length*.—About 1 cm.

*Strength*.—Moderately strong.

*Aspect*.—Initially upright to outwardly spreading.

*Texture*.—Densely pubescent; viscid.

*Color*.—Close to 143A.

Leaf description:

*Arrangement*.—Alternate, simple; sessile.

*Length*.—About 4.5 cm.

*Width*.—About 3.5 cm.

*Shape*.—Ovate.

*Apex*.—Acute.

*Base*.—Cuneate.

*Margin*.—Entire.

*Texture, upper and lower surfaces*.—Densely pubescent; viscid.

*Venation pattern*.—Pinnate; arcuate.

*Color*.—Developing leaves, upper surface: Close to 137A. Developing leaves, lower surface: Close to 143C. Fully expanded leaves, upper surface: Close to N137D; venation, close to N137C. Fully expanded leaves, lower surface: Close to 146A; venation, close to 143C.

Flower description:

*Flower arrangement and flowering habit*.—Relatively large single salverform flowers arising from leaf axils; freely flowering habit with usually about 17 flowers developing per plant; flowers face upright to outwardly.

*Fragrance*.—None detected.

*Natural flowering season*.—Plants typically beginning flowering about 6.5 weeks after planting; plants flower continuously from late spring, throughout the summer and into the autumn in The Netherlands.

*Flower longevity*.—Individual flowers last about five days on the plant; flowers persistent.

*Flower buds*.—Length: About 3.5 cm. Diameter: About 7 mm. Shape: Narrowly oblanceolate. Color: Close to 144C and 73A.

*Flower diameter*.—About 5.5 cm.

*Flower length* (*height*).—About 3.5 cm.

*Throat diameter*.—About 1.5 cm.

*Tube length*.—About 3 cm.

*Tube diameter*.—About 7 mm.

*Corolla*.—Arrangement: Five petals fused at the base and opening into a flared trumpet. Petal length from throat: About 2 cm. Petal lobe width: About 3 cm. Petal shape: Spatulate. Petal apex: Cuspidate. Petal margin: Entire. Petal lobe texture, upper and lower surfaces: Smooth, glabrous. Throat texture: Smooth, glabrous. Tube texture: Densely pubescent. Color: Petal, when opening, upper surface: Close to N66A. Petal, when opening, lower surface: Close to N66C. Petal, fully opened, upper surface: Center, close to 69D surrounded with close to N66C; color does not fade with development; venation, close to N144C. Petal, fully opened, lower surface: Center, close to N155B surrounded by close to 68B; venation, close to 144B. Throat: Close to 151D; venation, close to N144C. Tube: Close to 150C; venation, close to N144C.

*Calyx*.—Arrangement: One star-shaped calyx tube with five sepals per flower, sepals fused at the base. Sepal length: About 1.5 cm. Sepal width: About 5 mm. Sepal shape: Narrowly oblong. Sepal apex: Acute. Sepal base: Cuneate. Sepal margin: Entire. Sepal texture, upper and lower surfaces: Densely pubescent; viscid. Color, upper surface: Close to 143A. Color, lower surface: Close to 143C.

*Peduncles*.—Length: About 2 cm. Diameter: About 3 mm. Angle: About 40° from stem axis. Strength: Moderately strong. Texture: Densely pubescent; viscid. Color: Close to 144A.

*Reproductive organs*.—Stamens: Quantity per flower: Five. Filament length: About 2.2 cm. Filament color: Close to N155D and 157D. Anther shape: Broadly reniform. Anther length: About 2 mm. Anther color: Close to 158C. Pollen amount: Moderate. Pollen color: Close to 158D. Pistils: Quantity per flower: One. Pistil length: About 2 cm. Style length: About 1.9 cm. Style color: Close to 145C. Stigma shape: Flattened, three-lobed. Stigma color: Close to 143A.

Ovary color: Close to 145A. Fruits and seeds: Fruit and seed development have not been observed on plants of the new *Petunia*.

Garden performance: Plants of the new *Petunia* have been observed to have good garden performance and tolerate wind, rain and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Fipetfanangel' as illustrated and described.

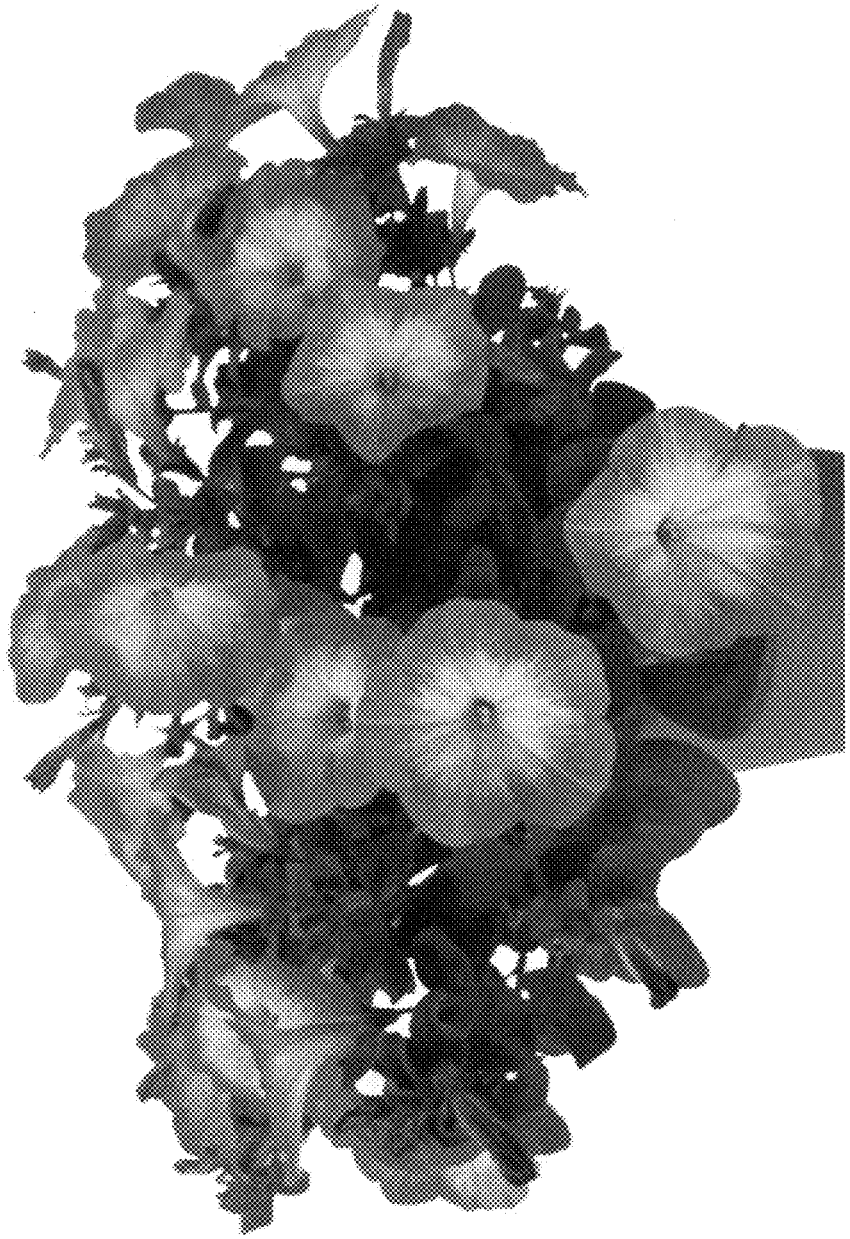

* * * * *